(12) United States Patent
Trager

(10) Patent No.: US 7,754,700 B2
(45) Date of Patent: Jul. 13, 2010

(54) COMPOSITION AND METHODS FOR ALLEVIATING SYMPTOMS OF NEUROTOXICITY

(76) Inventor: Seymour F. Trager, 1271 Sonatina Dr., Henderson, NV (US) 89052

( * ) Notice: Subject to any disclaimer, the term of this patent is extended or adjusted under 35 U.S.C. 154(b) by 1050 days.

(21) Appl. No.: 11/409,211

(22) Filed: Apr. 24, 2006

(65) Prior Publication Data

US 2007/0248690 A1    Oct. 25, 2007

(51) Int. Cl.
*A01N 43/04* (2006.01)
*A01N 43/26* (2006.01)
*A61K 31/385* (2006.01)
*A01N 37/12* (2006.01)
*A01N 37/44* (2006.01)
*A61K 31/44* (2006.01)
*A61K 31/522* (2006.01)
*A01N 59/20* (2006.01)
*A01N 59/06* (2006.01)
*A01N 59/02* (2006.01)

(52) U.S. Cl. .......... 514/52; 514/440; 514/561; 514/566; 514/356; 514/263.31; 514/553; 514/641; 514/682; 514/469; 424/638; 424/682; 424/702

(58) Field of Classification Search .......... 514/52, 514/440, 561, 566, 356, 263.31, 553, 641, 514/682, 469; 424/638, 682, 702
See application file for complete search history.

(56) References Cited

U.S. PATENT DOCUMENTS

| | | | |
|---|---|---|---|
| 5,886,042 A | 3/1999 | Yu et al. | |
| 6,093,417 A | 7/2000 | Petrus | |
| 6,268,351 B1 * | 7/2001 | Oberholtzer et al. | 514/46 |
| 6,294,520 B1 | 9/2001 | Naito | |
| 6,573,299 B1 | 6/2003 | Petrus | |
| 6,646,013 B1 | 11/2003 | Barker et al. | |
| 6,656,925 B2 | 12/2003 | Petrus | |
| 6,827,945 B2 | 12/2004 | Rosenbloom | |
| 6,831,103 B1 | 12/2004 | Ueda et al. | |
| 6,998,501 B1 | 2/2006 | Wright et al. | |
| 2002/0002146 A1 * | 1/2002 | Halevie-Goldman | 514/47 |
| 2002/0061870 A1 * | 5/2002 | Pearson et al. | 514/184 |
| 2004/0157783 A1 * | 8/2004 | McCaddon | 514/18 |
| 2004/0171624 A1 | 9/2004 | Ozeki et al. | |
| 2005/0043274 A1 | 2/2005 | Murad | |
| 2005/0090511 A1 | 4/2005 | Shibahara | |
| 2005/0129783 A1 * | 6/2005 | McCleary et al. | 424/646 |
| 2005/0163865 A1 | 7/2005 | Bieser et al. | |
| 2005/0261367 A1 | 11/2005 | Murad | |
| 2005/0266064 A1 | 12/2005 | McCarthy | |

FOREIGN PATENT DOCUMENTS

JP   2002-047183   2/2002
WO   WO 99/61038   12/1999

OTHER PUBLICATIONS

Kashii et al. (Investigative Ophthalmology and Visual Sci, Feb. 1994, 35, 2).*
Pyridoxal Phosphate -http://naturalpartners.silverw.com images/pdfs/AM0026.pdf—2003.*

* cited by examiner

*Primary Examiner*—Sreeni Padmanabhan
*Assistant Examiner*—Umamaheswari Ramachandran
(74) *Attorney, Agent, or Firm*—Kramer & Amado, P.C.

(57) ABSTRACT

A composition for alleviating symptoms associated with neurotoxicity. The composition may comprise compounds for preventing glutamate mediated neurotoxicity. The composition may include one or more of the following elements: at least one glutamate antagonist, at least one cAMP stimulating agent, at least one antioxidant, vitamin $B_{12}$, at least one transporter and at least one surfactant. The composition may be used in methods for alleviating tinnitus, Ménière's Disease and/or hearing loss.

9 Claims, No Drawings

COMPOSITION AND METHODS FOR ALLEVIATING SYMPTOMS OF NEUROTOXICITY

BACKGROUND

Neurotoxicity may be manifested in any number of debilitating symptoms. A number of these symptoms are manifested in the delicate physiology of the ear. In particular, the symptoms of neurotoxicity may be manifested auricularly as tinnitus, Ménière's Disease and hearing loss.

One such debilitating symptom of neurotoxicity is tinnitus. Tinnitus is the medical term for noise in the ears. People afflicted with tinnitus often hear ringing, hissing, chirping, buzzing, whistling or bell-like sounds in one or more ears. It is estimated that there are approximately 80 million sufferers of tinnitus worldwide.

Tinnitus may be caused by any number of known and unknown triggers. A common known cause of tinnitus is exposure to loud noises, either over a long period of time or brief intense events. Other known causes for triggering tinnitus include, but are not limited to severe head trauma, side effects from medication, sinus problems, respiratory infections, ear infections, wax build-up in the ears and certain types of tumors. Particular medications known to contribute to tinnitus include quinine, aspirin, aspartame, antibiotics and birth control pills.

A number of attempts have been made to alleviate the debilitating effects of tinnitus. For example a number of devices, such as maskers, hearing aids, white noise audio-tapes and other electronic devices are design to mask or drown-out the tinnitus pitch. Medical remedies include both surgical and pharmaceutical methods for alleviating tinnitus. Pharmaceutical treatments include tranquilizers, antidepressants, anti-inflammatory drugs, antibiotics, analgesic injections and/or antihypertension drugs.

Non-pharmaceutical supplements have also been used for tinnitus treatments. These include homeopathic drugs, herbal therapy, *Ginkgo biloba*, and lemon peel bioflavonoid. However, the treatments have not shown consistent effects in alleviating tinnitus.

Another symptom of neurotoxicity is Ménière's Disease. Ménière's disease is an abnormality of the inner ear causing a host of symptoms, including vertigo or severe dizziness, fluctuating hearing loss, and the sensation of pressure or pain in the affected ear. A number of triggers have been identified with Ménière's Disease, including environmental factors, such as noise pollution and viral infections, as well as biological factors, all of which may lead to neurotoxicity as discussed with regards to tinnitus above Previous attempts to alleviate the effects of Ménière's Disease have included dietary changes by reducing the body's retention of fluids (such as a low-salt or salt-free diet and no caffeine or alcohol) or medication. Changes in medications that either control allergies or improve blood circulation in the inner ear have been attempted with varying results. Eliminating tobacco use and reducing stress levels are other alternative methods for lessening the severity of the symptoms of neurotoxicity.

In addition to causing tinnitus and Ménière's Disease, neurotoxicity may also lead to hearing loss. Loud noises, particularly those characterized by a rapid rise in air pressure followed by a gradual decay to ambient levels, induce free-radical mediated oxidative stress in the middle ear. Therefore, noise induced neurotoxicity may lead to the increased prevalence of hearing loss, particularly for people who are exposed to loud noise on a regular basis.

Accordingly there is a need for providing a composition for alleviating the symptoms of neurotoxicity, such as, tinnitus, Ménière's Disease and/or hearing loss. The composition should alleviate the symptoms of the neurotoxicity, such as tinnitus, Ménière's Disease and/or hearing loss, in a person suffering therefrom without causing detrimental side effects. Furthermore, there is a need for a method of alleviating the symptoms caused by neurotoxicity, in particular tinnitus, Ménière's Disease and/or hearing loss.

SUMMARY

In an embodiment, a composition for alleviating symptoms of neurotoxicity comprises at least one glutamate antagonist, at least one cAMP stimulating agent, at least one antioxidant, and Vitamin $B_{12}$. In an alternative embodiment, a composition for alleviating symptoms of neurotoxicity comprises at least one glutamate antagonist, at least one antioxidant, and vitamin $B_{12}$. In an additional embodiment, a composition for alleviating symptoms of neurotoxicity comprises at least one glutamate antagonist and at least one surfactant. The composition may be administered for alleviating symptoms of neurotoxicity including, but not limited to, tinnitus, Ménière's Disease and/or hearing loss.

DETAILED DESCRIPTION

For simplicity and illustrative purposes, the principles are shown by way of examples of compositions and methods described. In the following description, numerous specific details are set forth in order to provide a thorough understanding of the examples. It will be apparent however, to one of ordinary skill in the art, that the examples may be practiced without limitation to these specific details. In other instances, well known methods and compositions are not described in detail so as not to unnecessarily obscure understanding of the examples.

The root neurological cause of tinnitus, Ménière's Disease and/or hearing loss often stems from neuronal injury. Neuronal injuries caused by trauma, infection, inflammation, drug reactions and/or ischemia trigger the release of toxic neurotransmitters. The neuronal injuries may be located in the peripheral nervous system or the central nervous system ("CNS") or in both the peripheral and central nervous systems. Otic or auricular neurological injury in particular may be manifested symptomatically as tinnitus, Ménière's Disease and/or hearing loss.

Glutamate is a specific neurotransmitter that has been particularly linked to neurotoxicity symptoms such as epilepsy, stroke and neurodegenerative conditions through the excitotoxicity pathway. In particular, neuronal injuries often trigger excess activation of glutamate receptors in the neurons leading to abnormally high amounts of glutamate being released into the synaptic space. By addressing the overstimulation of glutamate release resulting in neurotoxicity, the symptoms of neurotoxicity, particularly otic symptoms such as tinnitus, Ménière's Disease and/or hearing loss, may be alleviated.

In order to prevent neurotoxicity caused by excessive glutamate release, an embodiment of the composition contains at least one glutamate antagonist. The term antagonist is defined in the broad sense meaning a compound or substance that interferes with the physiological action of another. The interference is not limited to direct interference as the antagonist may act on or be part of a physiological or chemical process that is substantially removed from direct action on the antagonized compound. In the case of the glutamate antagonist of the composition, the antagonist may act to directly antagonize the action, binding, production and/or release of glutamate or promote another physiological compound or process that leads to the antagonism of the action, binding, production and/or release of glutamate.

In the composition containing at least one glutamate antagonist, the glutamate antagonist may include a number of different classes of compounds that either directly or indirectly antagonize glutamate. These classes may include, but are not limited to glutathione promoting agents, GABA stimulating agents, neurotransmitters and minerals. Specific glutamate antagonists may include, but are not limited to glutathione, theanine, n-acetylcysteine, α-lipoic acid, glycine, Gamma aminobuteric acid ("GABA"), L-glutamic acid, leucine, ibedenone, resveratrol or combinations thereof. In an embodiment of the invention the composition comprises one or more glutathione promoting agent, one or more GABA stimulating agent, one or more neurotransmitter, one or more mineral or combinations thereof.

In an embodiment of the composition the total amount of glutamate antagonists may be in the range of about 500-2,000 mg. In a preferred embodiment the total amount of glutamate antagonists may be in the range of about 750-1500 mg. Specific amounts of particular glutamate antagonists that may be formulated in one or more embodiments of the composition may include glutathione in the range of about 1-1,500 mg, GABA in the range of about of 2-1,500 mg, L-glutamic acid in the range of about 2-1,500 mg, leucine in the range of about 1-1,500 mg, or combinations thereof. In a preferred embodiment, the amount of glutathione may be in the range of about 20-100 mg. In a preferred embodiment the amount of GABA may be in the range of about 250-750 mg. In a preferred embodiment, the amount of L-glutamic acid may be in the range of about 25-250 mg. In a preferred embodiment, the amount of leucine may be in the range of about 20-100 mg.

The modifier "about" is used consistently throughout the application to mean a variance of plus or minus ten percent of the numbers or range that the term precedes.

An embodiment of the composition may include at least one glutathione promoting agent. The term glutathione promoting agent is broadly defined to encompass any compound that has been shown to directly or indirectly promote glutathione. Promoting glutathione is defined as increasing the production of, protecting the degradation of, activating a promoter of, and/or assisting in the action of glutathione, both directly and indirectly. In an embodiment of the invention, the glutathione promoting agent may include, but is not limited to taurine, N-acetylcysteine, theanine, α-lipoic acid or combinations thereof.

N-acetylcysteine and α-lipoic acid are antioxidant antagonists to glutamate and stimulate the production of glutathione. N-acetylcysteine, α-lipoic acid, and glutathione also have shown anti-inflammatory, anti-platelet aggregation effect and the ability to stimulate the production of c-AMP. Taurine acts as both an osmoregulator and a neuromodulator in the central nervous system in addition to stimulating glutathione production. Theanine, also known as gamma-glutamylethylamide, has been shown to promote glutathione production which protects against glutamate toxicity. Theanine also bears structural similarity to glutamate and has shown ability to directly compete with glutamate by binding to glutamate receptors.

In an embodiment of the composition, the total amount of glutathione promoting agents may be in the range of about 200-5,000 mg. In a preferred embodiment, the total amount of glutathione promoting agents may be in the range of 300-1,500 mg. Specific amounts of glutathione promoting agents that may be formulated in one or more embodiments of the formulation may include taurine in the range of about 100-5,000 mg, of N-acetylcysteine in the range of about 5-1000 mg, theanine in the range of about 5-500 mg, α-lipoic acid in the range of about 20-200 mg, or combinations thereof. The term α-lipoic acid refers to both the S and R forms of α-lipoic acid. In a preferred embodiment, the amount of taurine may be in the range of about 200-1,200 mg. In a preferred embodiment, the amount of N-acetylcysteine may be in the range of about 100-500 mg. In a preferred embodiment, the amount of theanine may be in the range of about 25-270 mg. In a preferred embodiment, the amount of α-lipoic acid may be in the range of about 50-150 mg.

An embodiment of the composition may include at least one GABA stimulating agent. In an embodiment of the invention, the GABA stimulating agent may include, but is not limited to niacin, pyrodoxal-5-phosphate, 5-hydroxy-tryptophan or combinations thereof.

Niacin is known in the art to stimulate the production of GABA. The term niacin includes niacin, nicotinamide and niacinamide. 5-hydroxy-tryptophan ("5-HTP") aids in the production of serotonin, dopamine, and epinephrine, all well known neurotransmitters. Furthermore, 5-HTP has been shown to stimulate production of GABA in the brain. Pyrodoxal-5-phosphate ("P-5-P"), GABA and glycine were found to be glutamate antagonists. Although the actual mechanism has not been confirmed, it is hypothesized that the compounds interfere with purine synthesis by inhibiting the conversion of formylglycinamide ribotide to formylglycinamidine, a reaction in which glutamine and/or glutamate is the donor of the amino group. Another possible mechanism of antagonizing glutamate is by activating glutamate dehydrogenase. Additionally, pyrodoxal-5-phosphate has been shown to stimulate GABA action.

In an embodiment of the composition the total amount of GABA stimulating agents, may range from about 5-1000 mg. In a preferred embodiment of the composition, the total amount of GABA stimulating agents may range from 5-100 mg. Specific amounts of one or more GABA stimulating agents that may be formulated in one or more of the embodiments of the composition may include niacin in the range of about 5-200 mg, P-5-P in the range of about 5-100 mg, 5-HTP in the range of about 5-300 mg or combinations thereof. In a preferred embodiment, the total amount of niacin may be in the range of about 10-40 mg. In a preferred embodiment, the total amount of P-5-P may be in the range of about 10-60 mg. In a preferred embodiment, the total amount of 5-HTP may be in the range of about 10-50 mg.

An embodiment of the composition may include at least one neurotransmitter. In an embodiment of the composition, the neurotransmitter may include, but is not limited to glycine, GABA or combinations thereof.

Glycine and GABA are among the most abundant of all neurotransmitters found in the central and peripheral nervous system which serve to regulate the excitability of almost all neurons. Glycine and GABA have inhibitory properties on central synaptic transmission. The inhibitory properties directly contrast and modulate the excitatory properties of glutamate. In particular, Glycine serves both inhibitory and excitatory functions of the central nervous system, and Glycine receptors are comprised of α-1 subunits which are efficiently gated by Taurine. In an embodiment of the invention, Glycine may refer to L-glycine.

In an embodiment of the composition, the total amounts of neurotransmitters may be about 50-2,000 mg. In a preferred embodiment, the amount of total amount of neurotransmitters may be about 75-1, 000 mg. Specific amounts of one or more neurotransmitters that may be formulated in one or more embodiments of the composition may include glycine in the range of about 50-1,500 mg, GABA in the range of about 100-1,500 mg or combinations thereof. In a preferred embodiment, the amount of glycine may range from 50-750 mg. In a preferred embodiment, the amount of GABA may range from about 250-750 mg.

An embodiment of the composition may include at least one mineral. In an embodiment of the composition, the mineral, may include, but is not limited to magnesium, zinc, copper and combinations thereof.

Magnesium is a calcium channel blocker that may block the calcium channels necessary for the release of glutamate. Furthermore, both magnesium and zinc act to stimulate vital enzymes involved in normal neurotransmission and thereby modulate the effects of excess glutamate. In compositions containing high amounts of zinc, copper may used to prevent toxicity associated with daily dosing of high amounts of zinc. Minerals such as magnesium often suffer from poor absorbability when administered orally. Magnesium's poor absorbability is one reason why it is often used as a laxative. In an embodiment of the composition, oral dosage forms containing magnesium may also contain surfactants and/or transporters for increasing the absorbability of magnesium and insuring proper transport to the required site of action.

In an embodiment of the composition, the total amount of minerals may be in the range of about 2-1,500 mg. In a preferred embodiment, the total amount of minerals may be in the range of about 50-500 mg. Specific amounts of one or more minerals that may be formulated in one or more embodiments of the composition may include magnesium in the range of about 20-1,200 mg, zinc in the range of about 2-200 mg, copper in the range of about 0.1-10 mg or combinations thereof. In a preferred embodiment, the amount of magnesium may be in the range of about 50-150 mg. In a preferred embodiment, the amount of zinc may be in the range of about 5-20 mg. In a preferred embodiment, the amount of copper may be in the range of about 0.25-5 mg.

An embodiment of the composition may include at least one cAMP stimulator. The term cAMP stimulator, includes, but is not limited to any compounds that stimulate cAMP directly and/or indirectly. Stimulation may include, but is not limited to increasing production, preventing degradation, or activating promoters, directly and/or indirectly. Forskolin activates adenylate cyclase which increases cyclic adenosine monophosphate (cAMP) which stimulates and regenerates damaged cells. In this manner forskolin has shown the ability to regenerate damaged nerve tissue. Forskolin has shown effects as a glutamate agonist. However, in an embodiment of the composition, the addition of theanine blocks forskolin agonism of glutamate by mimicking glutamate and blocking forskolin from binding with glutamate promoting mechanisms. Additionally, the therapeutic value of forskolin has been shown to be improved in combination with magnesium and zinc. Therefore an additional embodiment of the composition may include the combination of forskolin with magnesium and zinc.

In an embodiment of the composition, the total amount of cAMP stimulators may be in the range of about 10-1,000 mg. In a preferred embodiment, the total amount of cAMP stimulators may be in the range of about 10-200 mg. In an embodiment of the composition, the amount of forskolin may be in the range of about 10-500 mg. Other cAMP stimulators in the composition may include N-acetylcysteine, α-lipoic acid and glutathione. In a preferred embodiment, the amount of forskolin may be 15-100 mg.

An embodiment of the composition may include at least one antioxidant. In an embodiment of the composition, the antioxidant may include vinpocetine, PYCNOGENOL®, selenium, grape seed extract, ibedenone, resveratrol or combinations thereof.

Vinpocetine is a chemical ingredient synthesized from Vincamine, derived from Vina minor. Vinpocetine is an antioxidant and enhances blood flow to the brain and ears. Furthermore, vinpocetine inhibits the voltage neuronal sodium channels, indirectly inhibits some molecular cascades initiated by the rise of intracellular Ca+2 levels and to a lesser extent, inhibition of adenosine reuptake. Proanthocyanidin complexes found in natural substances provide powerful antioxidants. Proanthocyanidin antioxidants may be derived from grape seed extract or pine bark extract. A particular plant based antioxidant used in an embodiment of the composition may include pine bark extract with the trade name of PYCNOGENOL®. PYCNOGENOL®, available from Horphag Research, Ltd., is a specific mixture of procyanidins extracted from the bark of the French maritime pine, *Pinus maritima* (also known as *Pinus pinaster*). PYCNOGENOL® has demonstrated a number of antioxidant activities in the laboratory. These include scavenging of the superoxide radical anion, the hydroxyl radical, the lipid peroxyl radical, the peroxynitrite radical and singlet oxygen. Selenium is an essential trace element in human and animal nutrition involved in the defense against the toxicity of reactive oxygen species, in the regulation of thyroid hormone metabolism and the regulation of the redox state of cells. The antioxidant activity of selenium is mainly accounted for by virtue of its role in the formation and function of the selenium-dependent glutathione peroxidases (GSHPx). Glutathione peroxidases use reducing equivalents from glutathione to detoxify hydroperoxides. Ibedenone and resveratrol antagonize glutamate, stimulate nerve growth factor and are anti-inflammatory agents. In vitro testing has shown that ibedenone and resveratrol maintain homeostasis and accelerate wound healing by binding to transmemberase receptors in addition to their antioxidant properties. Additional in vitro studies have shown that ibedenone and resveratrol promote remyelation.

In an embodiment of the composition, the total amount of antioxidants may be in the range of about 1-2,500 mg. In a preferred embodiment of the composition, the total amount of antioxidants may be in the range of about 5-150 mg. Specific amounts of antioxidants that may be formulated in one or more embodiments of the composition may include vinpocetine in the range of about 1-500 mg, grape seed extract in the range of 1-2,000 mg, PYCNOGENOL® in the range of about 1-500 mg, selenium in the range of about 0.05 mcg-400 mcg, ibendeone in the range of about 5-1,000 mg, resveratrol in the range of about 1-500 mg or combinations thereof. In a preferred embodiment, the amount of vinpocetine may be in the range of about 2-100 mg. In a preferred embodiment, the amount of grape seed extract may be in the range of 5-500 mg. In a preferred embodiment, the amount of PYCNOGENOL® may be in the range of about 5-100 mg. In a preferred embodiment, the amount of selenium may be in the range of about 1-50 mcg. In a preferred embodiment, the amount of ibedenone may be in the range of about 20-200 mg. In a preferred embodiment, the amount of resveratrol may be in the range of 2-200 mg.

An embodiment of the composition may include Vitamin $B_{12}$. Vitamin $B_{12}$, a member of the B-vitamin family, is a collective term for a group of cobalt-containing compounds known as cobalamins. The principal cobalamins are cyanocobalamin, hydroxocobalamin and the two coenzyme forms of vitamin $B_{12}$, methylcobalamin and 5-deoxyadenosylcobalamin (adenosylcobalamin). The term Vitamin $B_{12}$, as defined in the composition, encompasses cyanocobalamin, hydroxocobalamin, methylcobalamin and/or 5-deoxyadenosylcobalamin. Vitamin $B_{12}$ is essential for the maintenance of the integrity of the nervous system. $B_{12}$ deficiencycan result in a number of neurological effects, including peripheral neuropathy and cognitive changes, including memory loss and dementia. Administration of $B_{12}$ successfully reverses mild memory impairment and peripheral neuropathy, if not advanced neurological deficits, in most elderly subjects deficient in the vitamin.

In an embodiment of the composition, the amount of vitamin $B_{12}$ may be in the range of about 1-500 mcg. In an alternative embodiment of the composition, vitamin $B_{12}$ may be methylcobalamin in the amount of about 2-200 mcg. In a preferred embodiment, the amount of vitamin $B_{12}$ may be in the range of about 50-200 mcg.

An embodiment of the composition may include a transporter or absorption enhancer. A number of the compounds of the composition have limited bioavailability or absorption through the gastrointestinal ("GI") tract. Several compounds also have limited ability to cross the blood-brain barrier. Furthermore, the compounds in the composition may show increased efficacy where they are transported to particular sites of action, such as, but not limited to, the cell mitochondria. Therefore, an embodiment of the composition may further include at least one transporter to assist in the absorption of the components of the composition thereby increasing bioavailability and/or preventing degradation in the GI tract. In an embodiment, one or more transporters may transport one or more components of the composition across the blood brain barrier or to particular intracellular destinations.

Any number of components of the various embodiments of the composition may benefit from combination with a transporter including, but not limited to magnesium, GABA, vinpocetine, P-5-P, theanine and/or glutathione. For example, it has been shown that the GI cells remove the phosphate molecules from P-5-P in the gut before it is absorbed. The use of transporters, such as proline, alanine and betaine HCl allow P-5-P to be absorbed before the degradation occurs. Glutathione is an example of another component that is degraded in the digestive tract. The term betaine includes betaine HCl among other variations.

Other compounds cannot cross the blood brain barrier. For example, theanine, which may be used as a direct glutamate antagonist or a GABA promoting agent, does not cross the blood-brain barrier. However, the addition of proline, leucine, and/or other known amino acid transporters may assist in the transport of theanine to the CNS. GABA is an example of another component that defuses very poorly across the blood brain barrier and benefits from the addition of one or more transporters.

In an embodiment of the composition, the total amount of transporters may be in the range of about 2-2,000 mg. In a preferred embodiment, the total amount of transporters is in the range of about 10-500 mg. In an embodiment of the composition, the amount of proline may be in the range of about 20-1,500 mg, the amount of betaine may be in the range of about 2-600 mg, the amount leucine may be in the range of about 200-600 mg, and the amount of alanine may be in the range of about 2-300 mg. In a preferred embodiment, the amount of proline may be in the range of about 5-200 mg. In a preferred embodiment, the amount of betaine may be in the range of about 10-400 mg. In a preferred embodiment, the amount of leucine may be in the range of about 10-100 mg. In a preferred embodiment, the amount of alanine may be in the range of about 10-100 mg.

An embodiment of the composition may further include surfactants or phospholipids. The surfactants may assist in transporting a number of the compounds of the composition from the GI tract into the blood or across the blood-brain barrier. Any number of components of the various embodiments of the composition may benefit from combination with a surfactant including, but not limited to magnesium, GABA, vinpocetine, P-5-P, theanine and/or glutathione. Surfactants may include compounds containing lecithin or derived from lecithin and/or other conventional surfactants. Compounds derived from lecithin or containing lecithin include but are not limited to the ULTRALEC®, available from ADM and ALCOLEC®, available from American Lecithin Company. Particular, types of the lecithin surfactant may be ULTRALEC-P®, available from ADM. Conventional surfactants may include, but are not limited to, any phospholipid well known in the art, the TWEEN® surfactants, including TWEEN® 20, TWEEN® 40, TWEEN® 60, TWEEN® 80 and TWEEN® 85, available from ICI Americas, Inc.; any polyethylene glycol surfactant and any sodium sulfate surfactant, such as sodium lauryl sulfate.

In an embodiment of the composition, the total amount of surfactants may be in the range of about 1-1000 mg. In a preferred embodiment, the total amount of surfactants may be in the range of 25-500 mg. In an embodiment of the composition, the amount of ALCOLEC® or the amount of ULTRALEC® may be in the range of about 1-500 mg. In a preferred embodiment, the amount of ALCOLEC® and/or ULTRALEC® may be in the range of about 50-300 mg.

The composition may be administered to a mammal orally, parenterally or rectally. In an embodiment, the composition may be in the form of an oral dosage form. The oral dosage form may include any oral dosage form known in the art, including, but not limited to capsules, tablets, pills, caplets, osmotic release dosage forms, solutions, powders, suspensions or dispersions. The composition may also be different dosage forms that in combination provide for the total composition for alleviating the symptoms of neurotoxicity. In an embodiment, the part of the combination may be in an oral dosage from that releases the active agents in the digestive tract, while a separate dosage form releases the active agents into the mucosal tissue, such as sublingually, buccally or nasally. In an embodiment, part of the combination may be released in the digestive tract while a second dosage form containing the remaining elements of the combination may be dose sublingually. The dosing may depend on whether or not the active agent is degraded in the digestive tract or is readily absorbed after digestion of the dosage form.

In an embodiment, the composition may be administered in one to ten doses during the course of twenty-four hours. In an alternative embodiment multiple doses may be administered concurrently to obtained the desired dosing schedule. In another embodiment the dosage forms may be immediate or controlled release depending on the active agents and the desired duration of effect.

The compositions may be administered for alleviating the symptoms of neurotoxicity including but not limited to tinnitus, Ménière's Disease and/or hearing loss. The composition may be administered one or more times a day, at particular intervals or depending on the severity of the symptoms. In an embodiment of the method for alleviating the symptoms of neurotoxicity, the composition may be administered one to five times a day in separate doses with each administration including one to three doses each time of administration.

EXAMPLES

Example 1

| INGREDIENTS | AMOUNT PER DOSE |
|---|---|
| Glutathione promoting agents | |
| taurine | 300 mg |
| N-acetylcysteine | 150 mg |
| theanine | 75 mg |
| α-lipoic acid | 75 mg |
| Total glutathione promoting agents | 600 mg |
| GABA stimulating agents | |
| P-5-P | 15 mg |
| Niacin | 20 mg |
| 5-HTP | 15 mg |
| Total GABA stimulating agents | 50 mg |
| Neurotransmitter | |
| glycine | 75 mg |
| Total neurotransmitters | 75 mg |
| Minerals | |
| magnesium | 100 mg |
| zinc | 7 mg |
| copper | 0.5 mg |
| Total minerals | 107.5 mg |
| cAMP stimulating agent | |
| forksolin | 25 mg |
| Total cAMP stimulating agents | 25 mg |
| Antioxidants | |
| PYCNOGENOL ® | 10 mg |
| vinpocetine | 8 mg |
| selenium | 10 mcg |
| Total antioxidants | 18.010 mg |
| Vitamin B$_{12}$ | 175 mcg |
| Transporters | |
| betaine | 200 mg |
| proline | 30 mg |
| alanine | 30 mg |
| Total transporters | 260 mg |
| Surfactants | |
| ULTRALEC-P ® | 50 mg |
| Total surfactants | 50 mg |
| Total weight of composition | 1,185.685 mg |

The above formulation was administered to two female patients suffering from tinnitus as the result of a bomb blast. The formulation was in the form of capsules. The patients took two capsules, three times per day and reported complete tinnitus relief from dose to dose. After the end of the dosing regime the patients reported a return of tinnitus, albeit at lower levels.

Example 2

The following example was administered in two dosage forms, a capsule form and a sublingual form.

| CAPSULE FORM | AMOUNT PER DOSE |
|---|---|
| Glutamate antagonist | |
| leucine | 50 mg |
| L-glutamic acid | 125 mg |
| Total glutamate antagonist | 175 mg |
| Glutathione promoting agents | |
| taurine | 500 mg |
| N-acetylcysteine | 250 mg |
| theanine | 135 mg |
| Total glutathione promoting agents | 885 mg |
| GABA stimulating agent | |
| Niacin | 25 mg |
| Total GABA stimulating agent | 25 mg |
| Minerals | |
| magnesium | 60 mg |
| zinc | 7 mg |
| copper | 0.5 mg |
| Total minerals | 67.5 |
| Antioxidants | |
| α-lipoic acid | 100 mg |
| PYCNOGENOL ® | 20 mg |
| Vinpocetine | 7.5 mg |
| Total antioxidants | 127.5 mg |
| Surfactant | |
| ULTRALEC-P ® | 200 mg |
| Total surfactant | 200 mg |
| Total weight of capsule form | 1,480 mg |

| SUBLINGUAL FORM | AMOUNT PER DOSE |
|---|---|
| Glutamate antagoinst | |
| glutathione | 50 mg |
| Total glutamate antagonist | 50 mg |
| GABA stimulating agent | |
| P-5-P | 30 mg |
| Total GABA stimulating agent | 30 mg |
| Vitamin B$_{12}$ | 175 mcg |
| Transporter | |
| Proline | 30 mg |
| Total amount of transporter | 30 mg |
| Surfactant | |
| ULTRALEC-P ® | 30 mg |
| Total surfactant | 30 mg |
| Total weight of sublingual form | 135.175 mg |

Seven subjects suffering from subjective Idiopathic Tinnitus were administered the formulation of Example 2. The combination was administered three times daily by ingesting the capsule and placing the sublingual form under the tongue.

Six of the seven subjects reported fairly good relief from tinnitus. One subject reported no change.

Example 3

| INGREDIENTS | AMOUNT PER DOSE |
|---|---|
| Glutathione promoting agents | |
| taurine | 1,000 mg |
| Total glutathione promoting agents | 1,000 mg |
| GABA stimulating agents | |
| P-5-P | 20 mg |
| Niacin | 20 mg |
| Total GABA stimulating agents | 40 mg |
| Neurotransmitters | |
| glycine | 500 mg |
| GABA | 500 mg |
| Total neurotransmitters | 1,000 mg |
| Minerals | |
| magnesium | 100 mg |
| zinc | 15 mg |
| Total minerals | 115 mg |
| Surfactant | |
| ALCOLEC ® | 200 mg |
| Total surfactant | 200 mg |
| Total weight of formulation | 2,355 mg |

Example 3 was administered as three doses per day to four subjects with high intensity tinnitus that had not responded to other formulas. One of the subjects showed a high degree of improvement. The three other subjects showed improvement over the previous formulations, but could still hear slight annoying noises.

The embodiments described above may also be administered for the alleviation and prevention of Ménière's Disease. In particular, the composition may be administered in a method for alleviating or preventing Ménière's Disease by daily dosing the composition one to five times a day. The method is particularly effective for people who have manifested Ménière's Disease as a result of environmental factors, such as noise pollution and viral infections, as well as biological factors. The method may including administering the composition to people suffering from vertigo or severe dizziness, fluctuating hearing loss, and the sensation of pressure or pain in the affected ear.

The formulations of the embodiments described above may also be administered for the alleviation and prevention of hearing loss. In particular, the composition may be administered in a method for alleviating or preventing hearing loss by daily dosing the composition one to five times a day. The method for preventing hearing loss is particularly useful for people who are exposed to loud noise on a regular basis, such as, but not limited to members of the military, those working in the music industry, those working in the construction or demolition industries and people attending concerts and/or sporting events. Furthermore, the composition may be used as a prophylactic from hearing loss caused by neurotoxicity associated with the loud noises of daily life, including, but not limited to street noise, sirens, portable music players, etc.

Although the present invention has been described in detail with particular reference to preferred embodiments thereof, it should be understood that the invention is capable of other different embodiments, and its details are capable of modifications in various obvious respects. As is readily apparent to those skilled in the art, variations and modifications can be affected while remaining within the spirit and scope of the invention. Accordingly, the foregoing disclosure, description, and examples are for illustrative purposes only, and do not in any way limit the invention, which is defined only by the claims.

What is claimed is:

1. A composition for treating tinnitus consisting of:
   at least one glutathione promoting agent;
   at least one GABA stimulating agent;
   at least one neurotransmitter;
   at least one mineral;
   at least one cAMP stimulating agent;
   at least one antioxidant;
   vitamin $B_{12}$;
   at least one surfactant; and
   at least one transporter.

2. The composition of claim 1, wherein the at least one glutathione promoting agent is selected from the group consisting of taurine, N-acetylcysteine, theanine, α-lipoic acid and mixtures thereof.

3. The composition of claim 1, wherein the at least one GABA stimulating agent is selected from the group consisting of pyrodoxal-5-phosphate, niacin, 5-hydroxy-tryptophan and mixtures thereof.

4. The composition of claim 1, wherein at least one neurotransmitter is glycine.

5. The composition of claim 1, wherein the at least one mineral is selected from the group consisting of magnesium, zinc, copper and mixtures thereof.

6. The composition of claim 1, wherein the at least one cAMP stimulating agent is forskolin.

7. The composition of claim 1, wherein the at least one antioxidant is selected from the group consisting of PYCNOGENOL®, vinpocetine, selenium and mixtures thereof.

8. The composition of claim 1, wherein the at least one transporter is selected from the group consisting of alanine, betaine, proline and a mixture thereof.

9. The composition of claim 1, wherein the at least one surfactant is selected from the group consisting of lecithin, a TWEEN surfactant, polyethylene glycol surfactant, a sodium sulfate surfactant and mixtures thereof.

* * * * *